(12) United States Patent  (10) Patent No.: US 8,063,226 B2
Jung et al.  (45) Date of Patent: Nov. 22, 2011

(54) PROCESS FOR PREPARING 2-AMINO-4-(HALOALKYL) PYRIDINE DERIVATIVES BY CYCLIZING SUITABLE NITRILE PRECURSORS WITH NITROGEN COMPOUNDS

(75) Inventors: Joerg Jung, Floersheim (DE); Sebastian Wuertz, Limburg (DE)

(73) Assignee: Archimica GmbH, Frankfurt am Main (DE)

( * ) Notice: Subject to any disclaimer, the term of this patent is extended or adjusted under 35 U.S.C. 154(b) by 0 days.

(21) Appl. No.: 12/721,616

(22) Filed: Mar. 11, 2010

(65) Prior Publication Data

US 2010/0234607 A1    Sep. 16, 2010

(30) Foreign Application Priority Data

Mar. 12, 2009  (DE) .......... 10 2009 012 471
Apr. 7, 2009   (DE) .......... 10 2009 016 374

(51) Int. Cl.
*C07D 213/73* (2006.01)
(52) U.S. Cl. .................................. 546/311
(58) Field of Classification Search .............. None
See application file for complete search history.

(56) References Cited

FOREIGN PATENT DOCUMENTS

EP   0 228 846 B1     4/1992
WO   WO 2007/000249 A1  1/2007

OTHER PUBLICATIONS

Tomcufcik et al., Heterocyclic Chemistry: Pyridine and Its Derivatives, p. III, Chap. 4, Aminopyridines, p. 3 (1961).*
Chem. Ber. (1936) 69, Nr. 12. pp. 2593-2605.
Huang, X. et al., *Organic Letters*, (2001) vol. 3, No. 21 pp. 3417-3419.
Dunn, A. D. et al., *Journal of Fluorine Chemistry* (1999) 93, pp. 153-157.
Mittelbach. et al., "*Syntheses with Nitriles, LXXV*[1]. The Reactivity of the Dimers of Malononitrile and Cyanoacetate with Dimethylformamide-dimethylacetal", *Monatshefte FürChemie*, (1987) 118, pp. 617-626 English Abstract.

* cited by examiner

*Primary Examiner* — Janet L. Andres
*Assistant Examiner* — Timothy R Rozof
(74) *Attorney, Agent, or Firm* — ProPat, L.L.C.

(57) ABSTRACT

A process in which a 2-aminopyridine derivative of the general formula II is obtained from open-chain nitrile precursor I or III by reaction with a nitrogen compound in a cyclization reaction is described.

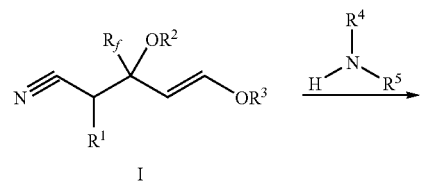

I

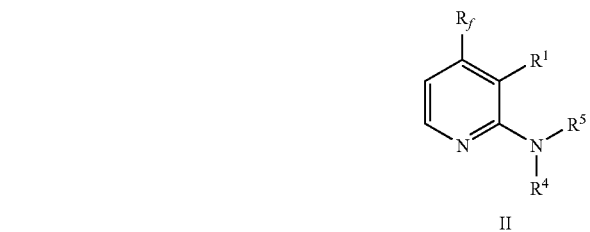

II

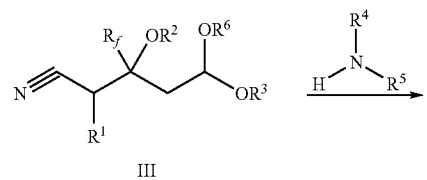

III

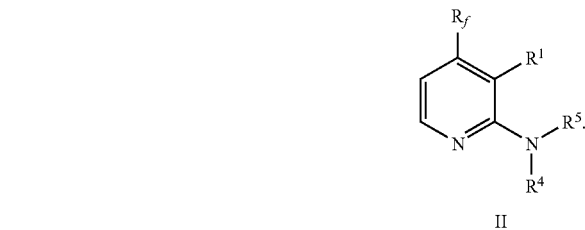

II

7 Claims, No Drawings

PROCESS FOR PREPARING 2-AMINO-4-(HALOALKYL) PYRIDINE DERIVATIVES BY CYCLIZING SUITABLE NITRILE PRECURSORS WITH NITROGEN COMPOUNDS

CROSS-REFERENCE TO RELATED APPLICATIONS

This application claims priority to German Patent Application 10 2009 012 471.3 filed Mar. 12, 2009 and German Patent Application 10 2009 016 374.3 filed Apr. 7, 2009, both of which are hereby incorporated herein by reference in their entirety.

FIELD OF THE INVENTION

The process according to the invention relates to the reaction of suitable nitrile precursors with nitrogen compounds to give the desired substituted pyridines. The starting materials are prepared generally by adding an alpha-metallated nitrile onto a carbonyl compound.

BACKGROUND OF THE INVENTION

Pyridines are important structural elements in a multitude of products in the chemical and pharmaceutical industry, and very many different processes for preparation are described in the literature. These can be divided roughly into processes in which the pyridine ring is built up, and those in which substituents are introduced (for example by electrophilic or nucleophilic substitution on the aromatic) or modified.

When 2-aminopyridine derivatives are required, they are usually prepared by introducing the amine substituent into a pyridine ring which is already present. Examples of such reactions are the Chichibabin reaction, i.e. the reaction of pyridines with sodium amide with elimination of sodium hydride, or the reaction of 2-halopyridines with nitrogen compounds (see, for example, Chem. Ber. 1936, 69, 2593 for the conversion of 3-amino-2-chloropyridine to 2,3-diaminopyridine).

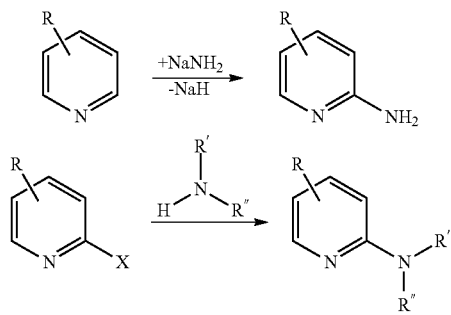

However, these reactions have the disadvantage that either quite drastic conditions are needed (Chichibabin reaction, reaction of 2-halopyridines with aqueous ammonia), or that expensive noble metals and ligands are required for the conversion in the more recent catalytic variants (e.g. Org. Lett. 2001, 3, 3417).

A further disadvantage of the reactions described is the fact that the corresponding precursors must be available for the synthesis of pyridines with difficult substitution, which is often not the case. Moreover, for the introduction of the desired substituent into the desired position, an industrially performable process has to be available, which allows the conversion of the precursor beyond the laboratory scale.

This is often not the case especially when perfluoroalkyl groups (usually trifluoromethyl groups) are to be introduced into the pyridine ring. Some reactions here are described in the literature, such as the reaction of iodopyridines with (trifluoromethyl)trimethylsilane

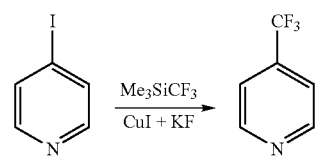

or the conversion of methyl groups to trifluoromethyl groups by the action of chlorine and hydrofluoric acid.

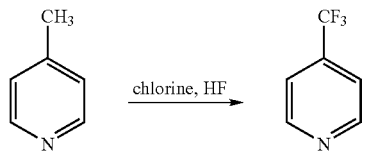

However, all processes known to date have disadvantages which make use for the preparation of the aminopyridines sought unattractive, or rule it out. For instance, the aminopyridines are unstable under the drastic conditions of the conversion of methyl to trifluoromethyl groups. It would thus first be necessary to prepare other pyridine derivatives, for example halopyridines, and to perform the conversion of halogen to amine in a separate step, which results in complex and expensive processes. Owing to the high costs of the starting materials, the introduction of a trifluoromethyl group by conversion of an iodopyridine with the aid of (trifluoromethyl)trimethylsilane is likewise hardly attractive for the industrial scale.

It was accordingly an object of the present invention to provide a process with the aid of which the desired 2-aminopyridine derivatives can be prepared with high flexibility with regard to the substitution pattern and with which it is possible to prepare especially perfluoroalkyl-substituted, preferably trifluoromethyl-substituted, 2-aminopyridines.

A similar process has already been described for 2-halopyridines (WO2007/000249, whose United States equivalent is United States Patent Application Publication No. 2008/0214825 A1). In this process, a nitrile is first metallated and then reacted with a suitable carbonyl compound to give the hydroxynitrile. The final ring closure is then effected under strongly acidic conditions with HX (HCl, HBr, HI) or inorganic esters of these substances (e.g. $SOCl_2$, $POCl_3$, $PCl_5$, $PBr_3$ etc.) under very strongly acidic conditions. This reaction is illustrated by way of example for the synthesis of 4-trifluoromethyl-2-chloropyridine.

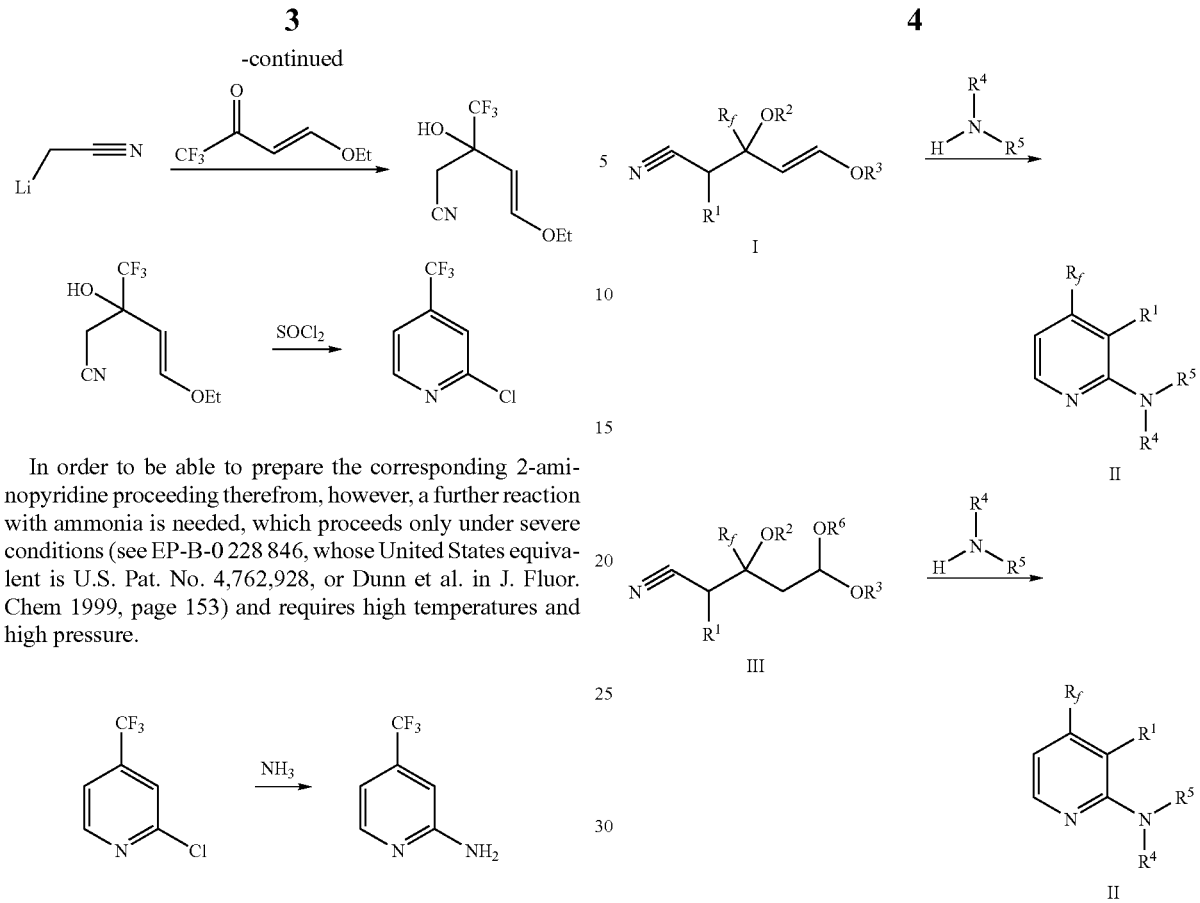

In order to be able to prepare the corresponding 2-aminopyridine proceeding therefrom, however, a further reaction with ammonia is needed, which proceeds only under severe conditions (see EP-B-0 228 846, whose United States equivalent is U.S. Pat. No. 4,762,928, or Dunn et al. in J. Fluor. Chem 1999, page 153) and requires high temperatures and high pressure.

SUMMARY OF ADVANTAGEOUS EMBODIMENTS OF THE INVENTION

Against this background, it was an object of the present invention to develop an economic process which is technically simple to perform for the preparation of 2-amino-4-(fluoroalkyl)pyridine derivatives.

DETAILED DESCRIPTION OF ADVANTAGEOUS EMBODIMENTS OF THE INVENTION

It has now been found that this object is achieved by direct reaction of the nitrile precursors described in WO2007/000249 with ammonia or other suitable nitrogen compounds.

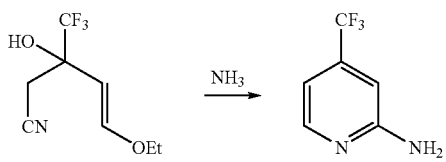

This is surprising because working under strongly acidic conditions in the above-described conversion to the halopyridine was considered to be crucial for the success.

This results in a general and flexible process with which substituted 2-aminopyridines, especially 2-aminopyridines with halogen-substituted alkyl substituents, can be prepared by building up the pyridine ring:

The different radicals in the above scheme are the following substituents:

$R_f$: $C_nH_{(2n+1-m)}X_m$
X: F, Cl, Br, where X is identical or different when m>1
n: positive integer from 1 to 8
m: positive integer from 1 to 2n+1
$R^1$: hydrogen, C1-C8-alkyl, C6-C14-aryl, C1-C13-heteroaryl, COOR, CN, $SO_2R$, SOR, $PO(OR)_2$, where these alkyl, aryl, heteroaryl, —COOR, —CN, —$SO_2R$, —SOR and —$PO(OR)_2$ radicals are unsubstituted or mono- or polysubstituted,
$R^2$: hydrogen or a protecting group for alcohols
$R^3$, $R^6$: C1-C8-alkyl, C1-C8-acyl, C6-C14-aryl, $R_3$silyl, where the alkyl, acyl and aryl radicals are unsubstituted or mono- or poly-substituted,
$R^4$,$R^5$: hydrogen, C1-C8-alkyl, C6-C14-aryl, C1-C13-heteroaryl, C1-C8-acyl, —$CONR_2$ where these alkyl, aryl, heteroaryl, acyl and —CONR2 radicals are unsubstituted or mono- or poly-substituted, or $R^4$ and $R^5$ together form a C4-C8-alkylene chain, where one $CH_2$ group may also be replaced by NH or O and where this C4-C8 chain is unsubstituted or mono- or poly-substituted
R: C1-C8-alkyl, C6-C14-aryl, C1-C13-heteroaryl.

"Alkyl" in the context of the invention—unless stated otherwise—is understood to mean a branched or unbranched $C_1$- to $C_{20}$-alkyl radical, preferably a $C_1$- to $C_{10}$-alkyl radical, especially methyl, ethyl, propyl, isopropyl, butyl, isobutyl, tert-butyl, pentyl or hexyl, more preferably methyl, ethyl, propyl or butyl.

Unless stated otherwise, "aryl" (or an "aromatic" radical) is a $C_6$- to $C_{14}$-aryl radical, especially phenyl, naphthyl, diphenyl. These aromatic substituents may in turn additionally bear alkyl or other aryl substituents.

Unless stated otherwise, "heteroaryl" (or a "heteroaromatic" radical) is a $C_5$- to $C_{13}$-aryl radical in which 1, 2 or more carbon atoms may be replaced independently by O, S, N, N-alkyl, especially furyl, thiophenyl, oxazolyl, thiazolyl, pyridyl, pyrimidyl, indolyl, quinoxalinyl or pyrrolyl.

"Halogen" or "halide" is, unless stated otherwise, understood to mean a fluorine, chlorine, bromine or iodine radical, preferably a bromine or chlorine radical.

Typical "protecting groups for alcohols" are, for example, acyl, alkyl, 2-tetrahydropyranyl or $R_3$silyl (where R=methyl, ethyl, propyl, tert-butyl). The particular R radicals may either all be the same or else be different.

"Mono- or polysubstituted" or "substituted" in the context of the invention means that the particular radical is monosubstituted or, if possible, di-, tri- or poly-halogen-substituted, preferably -chlorine- or -bromine-substituted, and/or -nitro-, -cyano-, -hydroxyl-, -alkyl-, -alkyloxy-, -aryl-, -aryloxy-, -arylalkyl-, -aryloxyalkyl-, arylalkyloxy-, -amino-, -monoalkylamino-, -dialkylamino-, -monoarylamino-, -diarylamino-, -alkylthio-, -arylthio-, -carboxyl-, -alkylcarbonyl- and/or -alkyloxycarbonyl-substituted.

The nitrile precursors required can be prepared by processes familiar to the person skilled in the art. Usually, however, the preparation according to one of the two schemes below, proceeding from the unsaturated ketone IV or from the acetal V, should be particularly economical:

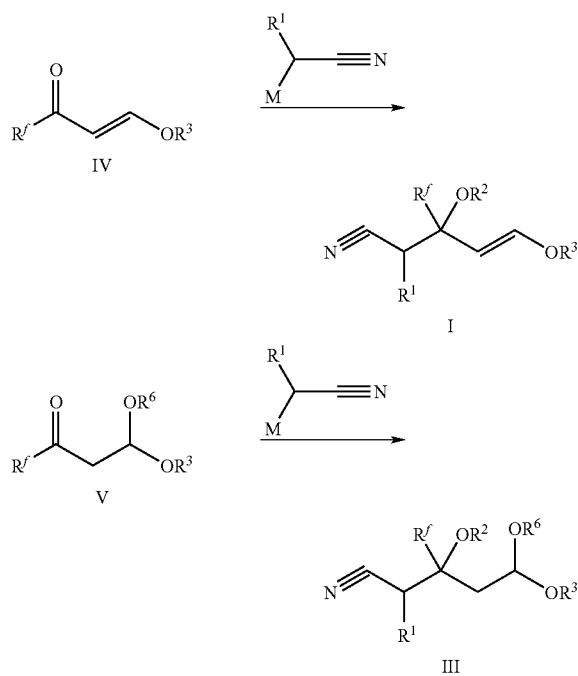

The definition of the R radicals is the same as explained above. In addition, M represents the following metals:
M: Li, Na, K, MgY, $Mg_{0.5}$, CaY, $Ca_{0.5}$, ZnY, $Zn_{0.5}$, CdY, $Cd_{0.5}$, Cu, $TiY_3$
Y: X (as defined above), I, OR, O—CO—R (with R as defined above).

To synthesize the nitriles required for the cyclization, as described above in the formula schemes, the route from the ketones IV or V and a salt of an acetonitrile derivative is generally the most favourable way. For this purpose, acetonitrile or a substituted derivative is first metallated in a suitable solvent and the salt formed is then reacted with a ketone of the general formula IV or V.

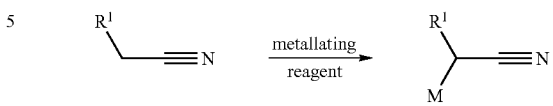

For this reaction, all solvents which can be used for metallation reactions are suitable. These are especially ethers such as tetrahydrofuran, 2-methyltetrahydrofuran, diethyl ether, diisopropyl ether, di-n-butyl ether, dioxane, 1,2-dimethoxyethane, diethylene glycol dimethyl ether, diethylene glycol di-n-butyl ether, tetraethylene glycol dimethyl ether or mixtures of these solvents with one another or with another inert solvent such as benzene, toluene, xylene, cyclohexane or petroleum ethers (hydrocarbon mixtures). In special cases, however, pure hydrocarbons such as benzene, toluene, xylene, cyclohexane or petroleum ether may also be suitable, or, in the case of strongly acidic acetonitrile derivatives ($R^1$ a strong acceptor substituent), even alcohols such as methanol, ethanol, isopropanol or butanols.

Useful metallating reagents include all bases which are sufficiently basic to abstract a hydrogen atom from the optionally substituted acetonitrile. In the case of acetonitrile itself or alkyl-substituted acetonitriles, principally very strong bases such as n-butyllithium, sec-butyllithium, t-butyllithium, n-hexyllithium, lithium N,N-diisopropylamide (LDA), lithium 2,2,6,6-tetramethylpiperidide (Li-TMP), lithium hexamethyl-disilazane (LiHMDS), sodium hexamethyldisilazane (NaHMDS) or potassium hexamethyldisilazane (KHMDS) are useful for this purpose. In the case of somewhat more acidic acetonitrile derivatives, for example aryl-substituted acetonitrile derivatives ($R^1$=aryl), bases such as sodium amide, lithium hydride, sodium hydride or potassium hydride are suitable in addition to those mentioned above. In the most strongly acidic acetonitrile derivatives ($R^1$=COOR, CN, $SO_2R$, SOR, $PO(OR)_2$), in addition to the strong bases already mentioned, alkoxides such as the lithium, sodium or potassium salts of methanol, ethanol or t-butanol are also suitable as bases.

The reaction conditions which should appropriately be observed in the metallation depend in turn on the acetonitrile derivatives used. For instance, in the case of the least acidic acetonitrile derivatives ($R^1$=alkyl or hydrogen), preference is given to working at temperatures below −25° C. and more preferably below −45° C., in order to prevent the decomposition of the salts formed. Owing to the greater stability of the salts formed, the more acidic acetonitrile derivatives can also be metallated at higher temperatures (when $R^1$=aryl up to approx. 0° C.; when $R^1$=CN, COOR, $SO_2R$, SOR also at room temperature or even higher).

The subsequent reaction with suitable ketones of the general formula IV or V is best carried out at the same temperature as the metallation and is generally effected by adding the ketones to the metallated acetonitrile or acetonitrile derivative. The addition sequence can, however, also be switched. Finally, the reaction mixture is usually worked up by neutralizing the base present with a suitable acid (e.g. sulphuric acid, acetic acid, citric acid, hydrochloric acid), and removing the salt formed with water. The product thus formed is purified by customary techniques such as distillation or crystallization or can often also be used in crude form in the next stage. In some cases, it may also be advantageous not to quench with a proton source but with other electrophiles. In that case, not the alcohols ($R^2$=H) but corresponding derivatives ($R^2$-alkyl, acyl, 2-tetrahydropyranyl, $R_3$silyl) form as starting materials for the cyclization.

The cyclization of the precursors I or III to the desired aminopyridine derivatives II can be effected with all suitable nitrogen compounds, i.e., with those in which $R^4$ and $R^5$, as specified above, are each independently hydrogen, alkyl, aryl, heteroaryl, acyl or —$CONR_2$. Both substituents may also be part of a ring system. The cyclization is generally performed in a suitable solvent. In the simplest case, this is the nitrogen compound itself or a mixture of the nitrogen compound with other solvents or solvent mixtures. Suitable solvents are all of those which do not hinder the reaction, i.e., for example, ethers (dioxane, THF, MTBE, diisopropyl ether, di-n-butyl ether), aromatics (toluene, xylene, benzene, chlorobenzene, anisole), alcohols (methanol, ethanol, propanol, isopropanol, butanol) or water.

The reaction is carried out by simply heating the precursors I or III with the nitrogen compounds in a solvent whose use is optional. Typical temperatures are 40° C. to 250° C., preferably 60° C. to 200° C. and more preferably 80° C. to 150° C. The addition of a catalyst is normally unnecessary to achieve the cyclization, but it is possible if required to add acidic or alkaline additives in order to accelerate the cyclization reaction. The acidic additives used are preferably salts of the nitrogen compounds used, more preferably salts of hydrochloric acid, sulphuric acid, phosphoric acid, p-toluenesulphonic acid, acetic acid or citric acid. Suitable basic additives are hydroxides, carbonates, oxides, alkoxides and other strongly basic compounds, preferably those which are more strongly basic than the nitrogen compounds used.

Depending on the properties of the product, the workup is effected by distillation or crystallization.

Example 1

Preparation of 5-ethoxy-3-hydroxy-3-(trifluoromethyl)pent-4-enenitrile as the Cyclization Precursor

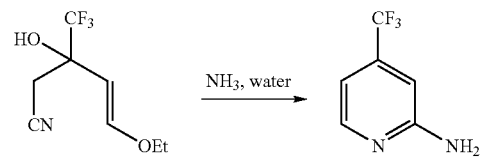

500 ml of 1,2-dimethoxyethane were cooled to −72° C. and admixed at this temperature first with 126 ml of n-BuLi (2.5 molar in hexane) and then, within 2 h, likewise at −72° C., with 12.8 g of acetonitrile. The mixture was then left to stir for a further 90 min in order to complete the formation of the anion. Subsequently, at −72° C., within 2 h, the mixture was admixed with a solution of 50 g of 1,1,1-trifluorobut-3-en-2-one (preparation according to Chem, Ber. 1989, 122, 1179-1186) in 100 ml of 1,2-dimethoxyethane, and then left to stir at this temperature for 1 h. Subsequently, the mixture was warmed to 0° C. and, for neutralization, admixed with a solution of 16.1 g of sulphuric acid (96%) in 50 ml of water.

Subsequently, 500 ml of toluene were added, the phases were separated and the aqueous phase was re-extracted twice with a further 100 ml of toluene. The combined organic phases were dried over sodium sulphate and then concentrated on a rotary evaporator. Finally, the product was distilled in a full oil-pump vacuum (approximately 0.2 mbar). It was thus possible to obtain 48.5 g of product (78%) of boiling point 95 to 110° C. This was identified on the basis of its mass spectrum (M+=209, further fragments at m/e=169, 141 and 71).

Example 2

Preparation of 2-amino-4-(trifluoromethyl)pyridine from 5-ethoxy-3-hydroxy-3-(trifluoromethyl)pent-4-enenitrile with Aqueous Ammonia

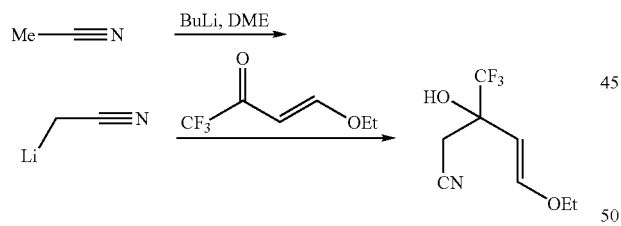

50 g of 5-ethoxy-3-hydroxy-3-(trifluoromethyl)pent-4-enenitrile were mixed with 600 g of aqueous ammonia (25%), and the resulting mixture was heated to 125° C. in an autoclave for 24 h, in the course of which a pressure of approx. 14 bar built up. Subsequently, the reaction mixture was cooled and the resulting biphasic mixture was extracted repeatedly with dichloromethane. The combined organic phases were cautiously concentrated by rotary evaporation, and the product was subsequently recrystallized from cyclohexane. 26.3 g of 2-amino-4-(trifluoromethyl)pyridine (68%) were thus obtained as a yellowish-brown solid. The spectroscopic data agreed with those reported in the literature (A. D. Dunn et al. in J. Fluorine Chem. 1999, 93, 153-157).

Example 3

Preparation of dimethyl(4-trifluoromethylpryridin-2-yl)amine from 5-ethoxy-3-hydroxy-3-(trifluoromethyl)pent-4-enenitrile with Aqueous Dimethylamine Solution

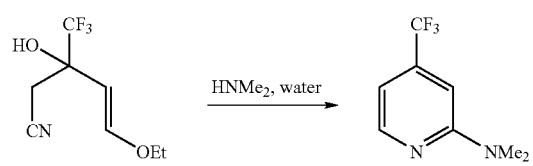

The procedure was analogous to Example 2, except that 600 g of aqueous dimethylamine solution (40%) were used instead of 600 g of aqueous ammonia. 28.1 g (62%) of product were thus isolated.

Example 4

Preparation of 5-ethoxy-3-hydroxy-2-phenyl-3-trifluoromethyl-pent-4-enenitrile as the Cyclization Precursor

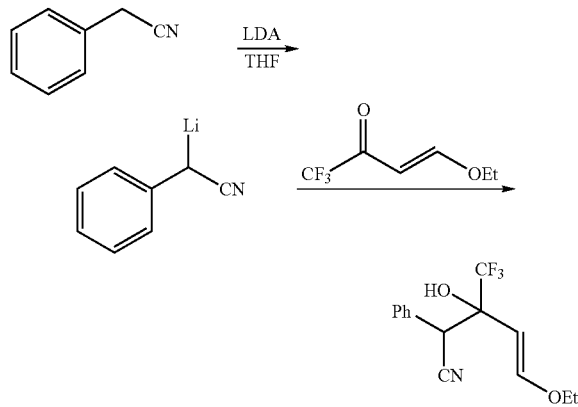

500 ml of THF were cooled to −72° C. and admixed at this temperature first with 31.9 g of diisopropylamine and then at the same temperature with 126 ml of n-BuLi (2.5 molar in hexane). Subsequently, 35.1 g of benzyl cyanide dissolved in a further 250 ml of THF were added dropwise within 1 h. The mixture was left to stir for a further 2 h in order to complete the formation of the anion. Subsequently, at −72° C., within 2 h, the mixture was admixed with a solution of 50 g of 1,1,1-trifluorobut-3-en-2-one and then left to stir at this temperature for 1 h. Subsequently, the mixture was warmed to 0° C. and, for neutralization, admixed with a solution of 16.1 g of sulphuric acid (96%) in 50 ml of water. Subsequently, 500 ml of toluene were added, the phases were separated and the aqueous phase was re-extracted twice with a further 100 ml of toluene. The combined organic phases were dried over sodium sulphate and then concentrated on a rotary evaporator. Approx. 77 g of a crude product were thus obtained, which was used thus in the next stage.

Example 5

Preparation of 3-phenyl-4-trifluoromethylpyridin-2-ylamine by Cyclization of 5-ethoxy-3-hydroxy-2-phenyl-3-trifluoromethylpent-4-enenitrile with Aqueous Ammonia

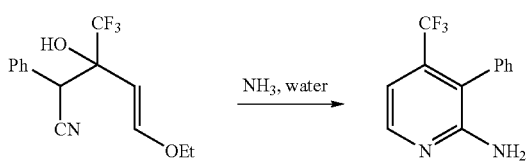

50 g of 5-ethoxy-3-hydroxy-2-phenyl-3-trifluoromethyl-pent-4-enenitrile were mixed with 600 g of aqueous ammonia (25%), and the resulting mixture was heated to 125° C. in an autoclave for 24 h. Subsequently, the reaction mixture was cooled and the resulting biphasic mixture was extracted repeatedly with dichloromethane. The combined organic phases were concentrated by rotary evaporation and the product was subsequently recrystallized from heptane. 24.1 g of 3-phenyl-4-trifluoromethylpyridin-2-ylamine (52% over both stages) were thus isolated.

That which is claimed:

1. A process for preparing 2-aminopyridine derivative of the general formula II comprising reacting an open-chain nitrile precursor I or III with a nitrogen compound in a cyclization reaction:

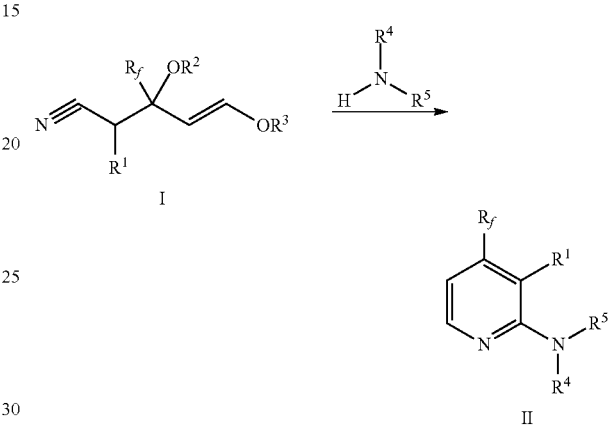

where the substituents $R^1$ to $R^6$ and $R^f$ are each defined as follows:
$R_f$: $C_nH_{(2n+1-m)}X_m$
X: F, Cl, Br, where X is identical or different when m>1
n: positive integer from 1 to 4;
m: positive integer from 1 to 2n+1
$R^1$: hydrogen, C1-C4-alkyl, or C6-aryl,
$R^2$: hydrogen or a protecting group for alcohols
$R^3,R^6$: C1-C4-alkyl,
$R^4,R^5$: hydrogen,
R: C1-C8-alkyl, C6-C14-aryl, C1-C13-heteroaryl.

2. A process according to claim 1, wherein the cyclization reaction comprises reacting the enol ether open-chain nitrile precursor I.

3. A process according to claim 2, wherein said process further comprises forming the enol ether open-chain nitrile precursor I by reacting ketone IV with metallated acetonitrile or a metallated acetonitrile derivative according to the following reaction scheme:

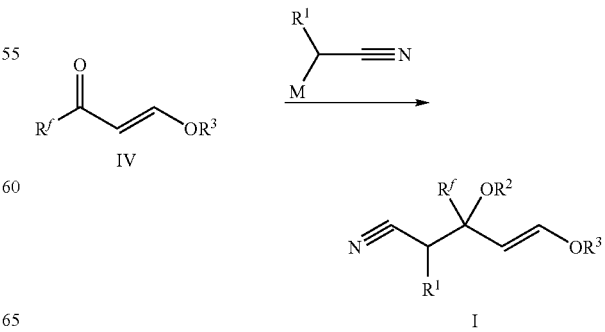

where

M is Li, Na, K, MgY, Mg$_{0.5}$, CaY, Ca$_{0.5}$, ZnY, Zn$_{0.5}$, CdY, Cd$_{0.5}$, Cu, TiY$_3$ and Y is X or I, OR, O—CO—R.

4. A process according to claim 1, wherein $R^2$ is hydrogen.

5. A process according to claim 1, wherein the $R_f$ radical is trifluoromethyl.

6. A process according to claim 1, wherein the nitrogen compound is an amine.

7. A process according to claim 1, wherein the nitrogen compound is ammonia.

* * * * *